United States Patent [19]

Regnier

[11] Patent Number: 5,664,592

[45] Date of Patent: Sep. 9, 1997

[54] FLOSSING DEVICE

[76] Inventor: Todd F. Regnier, 1106 Vista Hts., Victoria, B.C., Canada, V8T2H4

[21] Appl. No.: 631,982

[22] Filed: Apr. 15, 1996

[51] Int. Cl.$^6$ .................................................. A61G 15/00
[52] U.S. Cl. ...................... 132/325; 132/323; 132/324; 132/326; 132/327
[58] Field of Search ....................... 132/321, 323, 132/324, 325, 326, 327, 328, 329; 433/161

[56] References Cited

U.S. PATENT DOCUMENTS

| D. 251,074 | 2/1979 | Schiff | 132/323 |
|---|---|---|---|
| 1,916,653 | 7/1933 | Bodde | 132/326 |
| 5,105,840 | 4/1992 | Giacopuzzi | 132/325 |
| 5,232,002 | 8/1993 | McClallen | 132/323 |

FOREIGN PATENT DOCUMENTS 1095460  12/1960  Germany .............................. 132/323

*Primary Examiner*—Gene Mancene
*Assistant Examiner*—Pedro Philogene

[57] ABSTRACT

The present invention relates to a device to aid a user in flossing their teeth. In its broadest context, the present invention includes a supply arm, with an associated floss supply assembly, and a take-up arm, with an associated floss take-up assembly. Furthermore, each of the arms includes a number of recesses formed approximate its rearward end. A band is included which is adapted to be fitted into a pair of the recesses. The band is utilized to place the device in its loading orientation, or alternatively its use orientation.

4 Claims, 3 Drawing Sheets

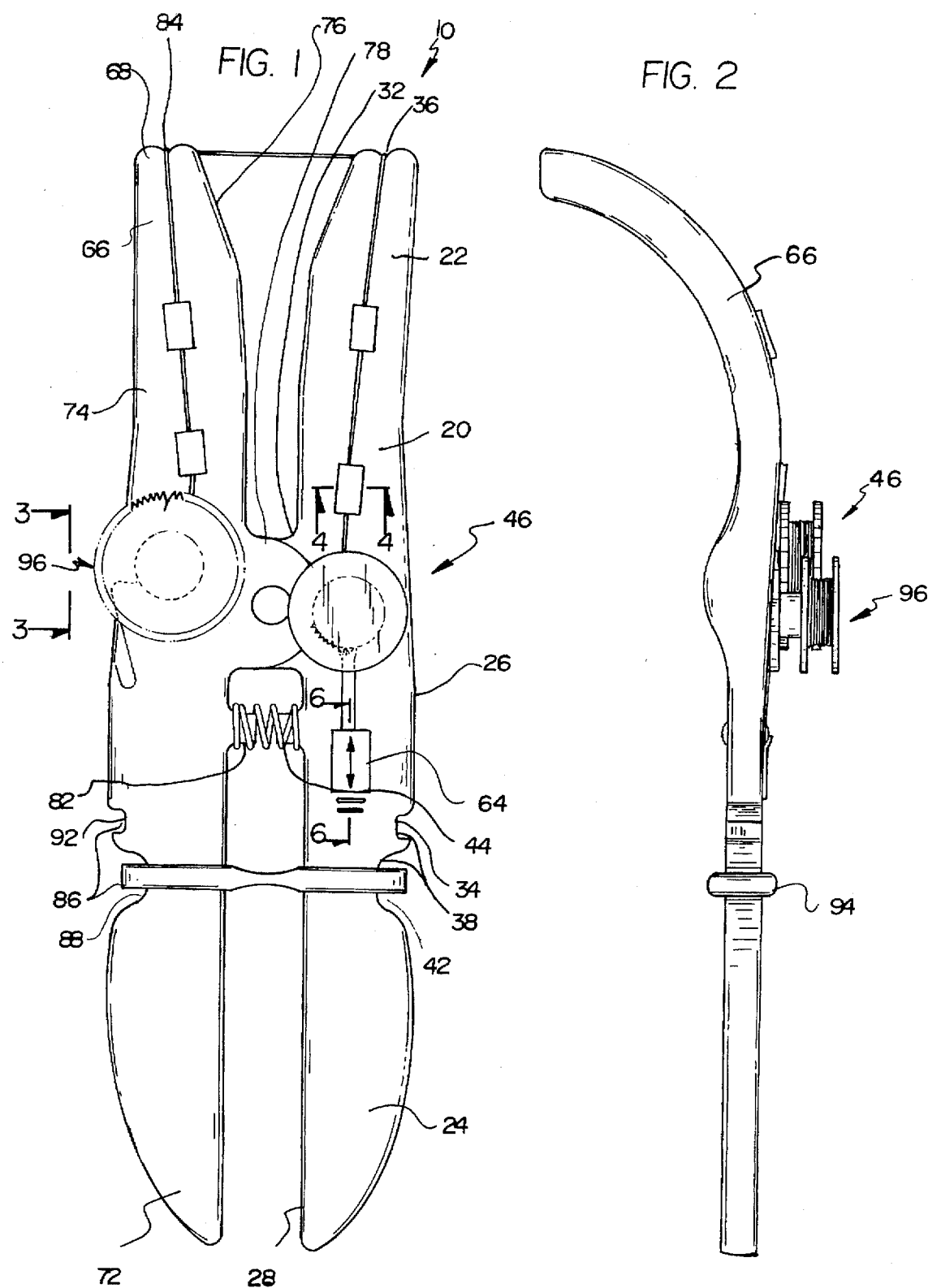

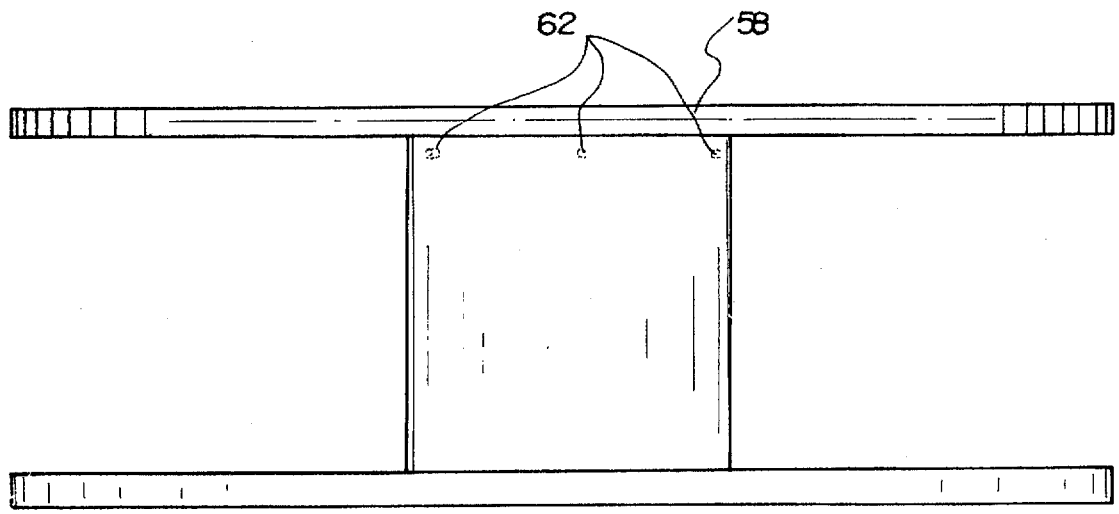
FIG. 3
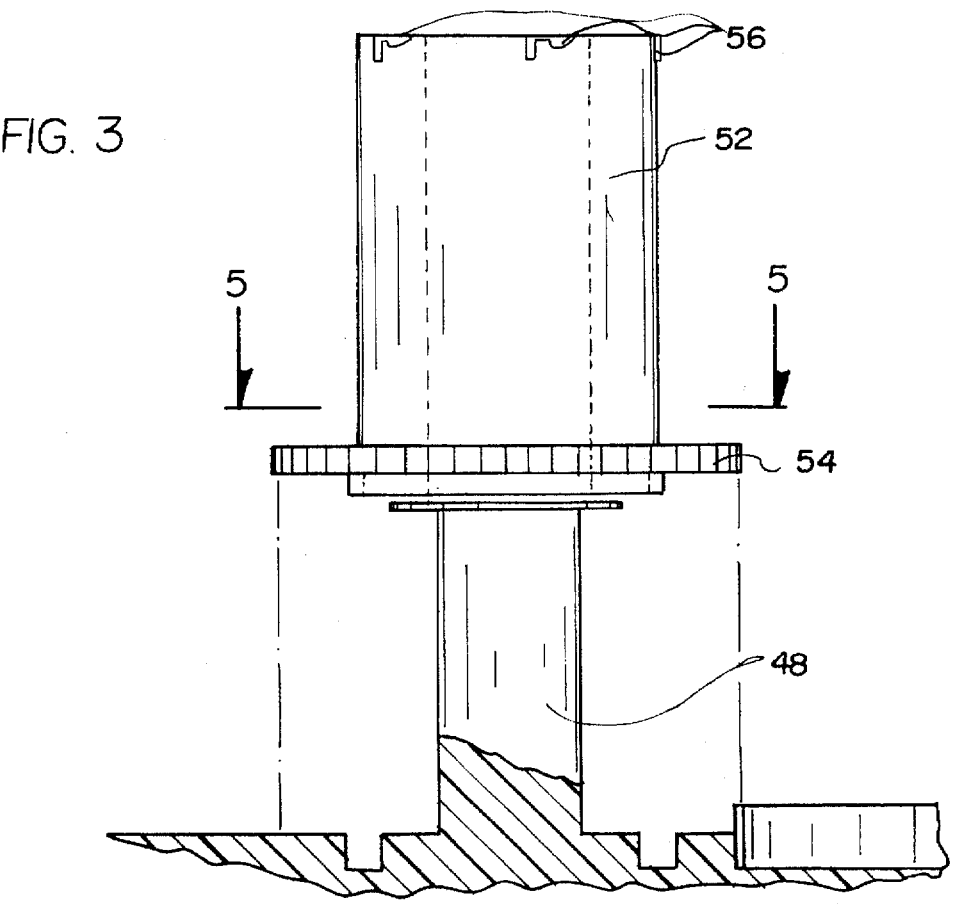
FIG. 4
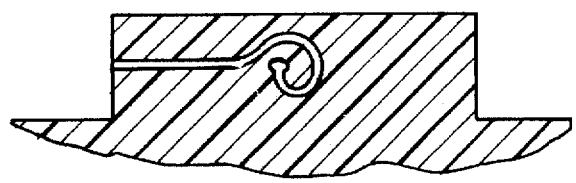

FLOSSING DEVICE

BACKGROUND OF THE INVENTION

1. Field of the Invention

The present invention relates to flossing device and more particularly pertains to such a device with simplified threading of the floss.

2. Description of the Prior Art

The use of floss tools is known in the prior art. More specifically, floss tools heretofore devised and utilized for the purpose of cleaning the teeth and gums are known to consist basically of familiar, expected, and obvious structural configurations, notwithstanding the myriad of designs encompassed by the crowded prior art which has been developed for the fulfillment of countless objectives and requirements.

For example U.S. Pat. Nos. 5,188,133 to Romanus; 5,197,498 to Steward; Des. 339,884 to Hartman; 5,301,698 to Ballard; 5,335,798 to Bonwell et al.; and 5,201,330 to Won all disclose various flossing tool devices.

In this respect, the flossing device according to the present invention substantially departs from the conventional concepts and designs of the prior art, and in doing so provides an apparatus primarily developed for the purpose of simplifying the threading process.

Therefore, it can be appreciated that there exists a continuing need for new and improved flossing device which can be used for flossing ones teeth. In this regard, the present invention substantially fulfills this need.

SUMMARY OF THE INVENTION

In view of the foregoing disadvantages inherent in the known types of floss tools now present in the prior art, the present invention provides an improved flossing device. As such, the general purpose of the present invention, which will be described subsequently in greater detail, is to provide a new and improved flossing device and method which has all the advantages of the prior art and none of the disadvantages.

To attain this, the present invention essentially comprises a flossing device having a floss loading orientation and a floss use orientation. The device comprising a supply arm having a forward end, a rearward end and an intermediate extent therebetween, the supply arm further includes an outer edge, an inner edge an upper surface and a lower surface. A semicircular extension is formed on the inner edge of the supply arm at the intermediate extent. A spring support is formed on the inner edge of the supply arm intermediate the semicircular extension and the rearward end. A floss channel is formed within the upper surface of the supply arm and extends from adjacent the semicircular extension to the forward end. A number of floss guides are formed along the floss channel, and a circular recess formed within the upper surface of the supply arm adjacent the semicircular extension. The circular recess serves to define an interior area. A number of recess are formed within the outer edge of the supply arm in between the intermediate extent and the rearward end. At least one of these recesses constitutes a loading orientation recess and at least one of the recesses constitutes a use orientation recess. A floss supply assembly is associated with the supply arm. This floss supply assembly comprises a shaft integrally formed within the interior area of the supply arm. A cylindrical geared shaft cover which has an upper peripheral edge and a lower peripheral edge is included in the assembly. A gear is formed integrally with the shaft cover adjacent the lower peripheral edge. A plurality of locking notches are formed within the upper peripheral edge of this element. The shaft cover is positioned over the shaft such that the lower peripheral edge fits into the circular recess of the supply arm. The supply spool has an upper circular plate, a lower circular plate and a cylindrical extent therebetween. The cylindrical extent has an interior area, and a plurality of locking protrusions extending from the interior area of the cylindrical extent of the supply spool. The number and position of these protrusions correspond to the number and position of the locking notches. The supply spool is adapted to be fitted over the shaft cover such that the locking notches engage the locking protrusions. A supply of dental floss is supplied upon the supply spool. A thumb slide is slidably provided within the upper surface of the supply arm adjacent the shaft. The thumb slide has a forward gear engaging end. The thumb slide has a first orientation wherein the first end is engaged with the gear of the shaft cover and a second orientation wherein the first end is disengaged from the gear of the shaft cover. The device further includes a take-up arm having a forward end, a rearward end and an intermediate extent therebetween. The take-up arm further includes an outer edge, an inner edge an upper surface and a lower surface. A semicircular extension is formed on the inner edge of the take-up arm at the intermediate extent. A spring support is formed on the inner edge of the take-up arm intermediate the semicircular extension and the rearward end. Furthermore, a floss channel is formed within the upper surface of the take-up arm and extends from adjacent the semicircular extension to the forward end. A number of floss guides are formed along the floss channel. A circular recess is formed within the upper surface of the take-up arm adjacent the semicircular extension. The circular recess defines an interior area, and a number of recess are formed within the outer edge of the take-up arm in between the intermediate extent and the rearward end, at least one of the recesses constitutes a loading orientation recess and at least one of the recesses constitutes a use orientation recess. A floss take-up assembly is associated with the take up arm. The floss take-up assembly comprises a shaft integrally formed within the interior area of the take-up arm, and a cylindrical geared shaft cover having an upper peripheral edge and a lower peripheral edge. A gear is formed integrally with the shaft cover adjacent the lower peripheral edge. A plurality of locking notches are formed within the upper peripheral edge. The shaft cover is positioned over the shaft such that the lower peripheral edge fits into the circular recess of the take-up arm. A take-up spool is included having an upper circular plate, a lower circular plate and a cylindrical extent therebetween. The cylindrical extent has an interior area, and a plurality of locking protrusions extend from the interior area of the cylindrical extent of the take-up spool. The number and position of these protrusions corresponds to the number and position of the locking notches. The take-up spool is adapted to be fitted over the shaft cover such that the locking notches engage the locking protrusions. The supply arm and take-up arm are pivotally interconnected by way of the semicircular extension of the supply arm and the semicircular extension of the take-up arm. A spring serves to interconnect the spring support of the supply arm and the spring support of the take-up arm. Furthermore, a band is adapted to be positioned within one of the recesses of the supply arm and one of the recesses of the take-up arm. The device being in a loading orientation when the band is positioned within loading orientation recesses, and the device being in a use orientation when the band is positioned within use orientation recesses.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved flossing device which have all the advantages of the prior art floss tools and none of the disadvantages.

It is another object of the present invention to provide new and improved flossing device which may be easily and efficiently manufactured and marketed.

It is further object of the present invention to provide new and improved flossing device which are of durable and reliable constructions.

An even further object of the present invention is to provide new and improved flossing device which are susceptible of a low cost of manufacture with regard to both materials and labor, and which accordingly are then susceptible of low prices of sale to the consuming public, thereby making such flossing device economically available to the buying public.

Still yet another object of the present invention is to provide new and improved flossing device which provide in the apparatuses and methods of the prior art some of the advantages thereof, while simultaneously overcoming some of the disadvantages normally associated therewith.

Even still another object of the present invention is to provide a floss tool which is easy to use.

Lastly, it is an object of the present invention to provide a new and improved device to aid a user in flossing their teeth. In its broadest context, the present invention includes a supply arm, with an associated floss supply assembly, and a take-up arm, with an associated floss take-up assembly. Furthermore, each of the arms includes a number of recesses formed approximate its rearward end. A band is included which is adapted to be fitted into a pair of the recesses. The band is utilized to place the device in its loading orientation, or alternatively its use orientation.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a top view of the preferred embodiment of the flossing device constructed in accordance with the principles of the present invention.

FIG. 2 is a side view of the device.

FIG. 3 is a view of the assembly employed with either the supply assembly or the take-up assembly.

FIG. 4 is a view taken along lines 4—4 of FIG. 1.

The same reference numerals refer to the same parts through the various Figures.

DESCRIPTION OF THE PREFERRED EMBODIMENT

Figure 5:
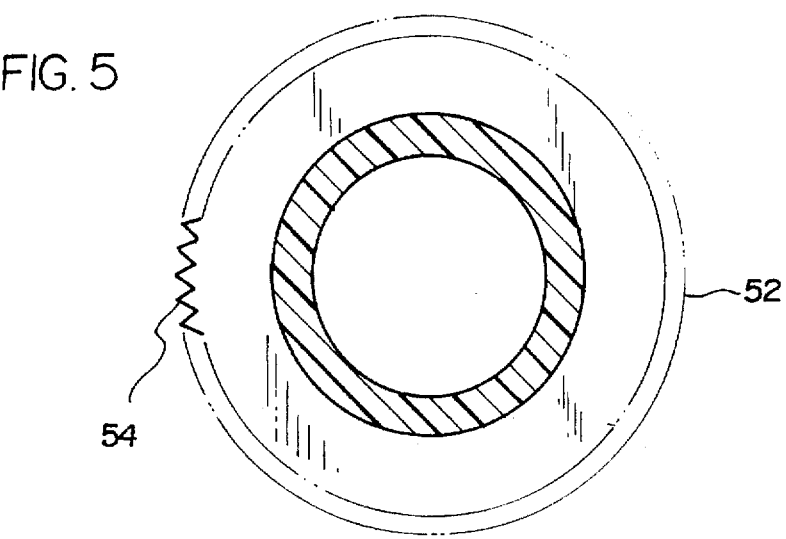
FIG. 5 is a view taken along lines 5—5 of FIG. 3.
Figure 6:
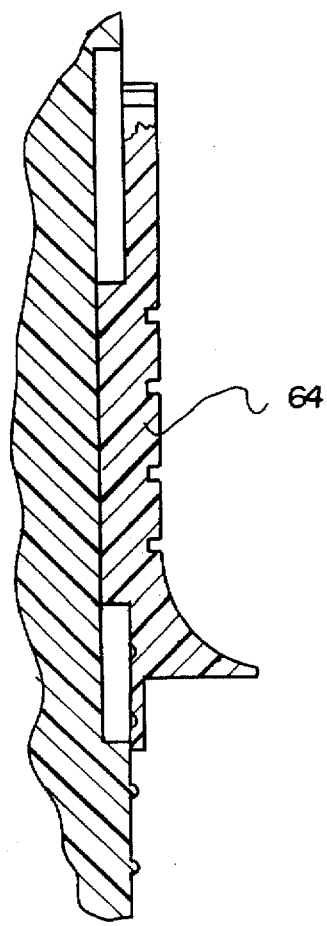
FIG. 6 is a view of the thumb slide of the present invention.

With reference now to the drawings, and in particular to FIG. 1 thereof, the preferred embodiment of the new and improved flossing device embodying the principles and concepts of the present invention and generally designated by the reference numeral 10 will be described.

The present invention relates to a device to aid a user in flossing their teeth. In its broadest context, the present invention includes a supply arm, with an associated floss supply assembly, and a take-up arm, with an associated floss take-up assembly. Furthermore, each of the arms includes a number of recesses formed approximate its rearward end. A band is included which is adapted to be fitted into a pair of the recesses. The band is utilized to place the device in its loading orientation, or alternatively its use orientation. The details of the components of the present invention, and the manner in which they interrelate, will be described in greater detail hereinafter.

THE SUPPLY ARM

The supply arm 20 is defined by a forward end 22, a rearward end 24 and an intermediate extent therebetween. The supply arm 20 is further defined by an outer edge 26, an inner edge 28, an upper surface and a lower surface. As is illustrated in FIG. 2, the forward end 22 of the supply arm 20 is curved. This curvature allows a more efficient use of the device while flossing. A semicircular extension 32 is formed upon the inner edge 28 of the supply arm 20 at the intermediate extent. Additionally, a spring support 44 is formed upon the inner edge 28 of the supply arm 20 intermediate the semicircular extension 32 and the rearward end 24. The function of the semicircular extension 32 and the spring support 44 will be described in greater detail hereinafter.

The supply arm 20 further includes a floss channel 36 formed within its upper surface. This floss channel 36 extends from adjacent the semicircular extension 32 to the forward end 22 of the arm. The floss channel 36 is essentially a groove which aids in the routing of the dental floss. To further aid the routing of the dental floss, a number of floss guides are formed along the length of the floss channel 36. Each of these floss guides takes the form of a block with an interior passageway which keeps any dental floss in alignment with the channel. A circular recess is formed within the upper surface of the supply arm 20 adjacent the semicircular extension. This circular recess defines an interior area. The circular recess and corresponding interior area will be described in greater detail in association with the floss supply assembly. The supply arm 20 further includes a number of recess formed within its outer edge 26 in between the intermediate extent and the rearward end 24. At least one of these recesses 38 constitutes a loading orientation recess, and at least one of the recesses 38 constitutes a use orientation recess. In the preferred embodiment, there are two such recesses 38, one being the loading orientation recess 42 and the other being the use orientation recess 34. The exact function of these recesses 38 will be described in greater detail hereinafter.

FLOSS SUPPLY ASSEMBLY

As indicated hereinabove, the supply arm includes a floss supply assembly 46. This floss supply assembly 46 includes a shaft 48 integrally formed within the interior area of the supply arm. A cylindrical geared shaft cover 52, in part defined by an upper peripheral edge and a lower peripheral edge, is adapted to be positioned over the shaft 48. The shaft cover 52 includes a gear 54 integrally formed with the shaft cover 52 adjacent the lower peripheral edge. Furthermore, a plurality of locking notches 56 are formed within the upper peripheral edge of the cover. This shaft cover 52 is positioned over the shaft 48 such that the lower peripheral edge fits into the circular recess of the supply arm. The supply assembly further includes a supply spool 58. This supply spool 58 is defined by an upper circular plate, a lower circular plate and a cylindrical extent therebetween. The cylindrical extent includes an interior area and a plurality of locking protrusions 62 which extending from the interior area of the cylindrical extent. The number and position of these protrusions corresponding to the number and position of the locking notches 56.

Thus, the supply spool 58 is adapted to be fitted over the shaft cover 52 such that the locking notches 56 engage the locking protrusions 62. More specifically, the supply spool 58 is adapted to be fitted over the shaft cover 52 such that the protrusions engage the corresponding recesses. Each of the recess includes a 90 degree bend such that the supply spool 58 can be rotated slightly to lock the supply spool 58 upon the shaft cover 52. Furthermore, a spring can be utilized in between the supply spool 58 and the shaft cover 52 to, in effect, bias the supply spool 58 into a locked orientation. Thus, when a user wishes to position a supply spool 58 over the shaft cover 52 they first place the supply spool 58 over the shaft cover 52 against the bias of the springs. Next, the supply spool 58 is rotated slightly relative to the shaft cover 52. This slight rotation locks the supply spool 58 in place. The supply spool 58 contains a supply of dental floss wound about its cylindrical extent.

In order to appropriately control the feeding of dental floss from the supply spool 58 a thumb slide 64 is employed. This thumb slide 64 is slidably positioned within the upper surface of the supply arm adjacent the shaft 48. The thumb slide 64 includes a forward gear engaging end. This gear engaging end employs a plurality of prongs each of which are adapted to engage a discrete location upon the gear 54. The thumb slide 64 has a first orientation wherein the first end is engaged with the gear 54 of the shaft cover 52, and a second orientation wherein the first end is disengaged from the gear 54 of the shaft cover 52. Thus, when the thumb slide 64 is in the first orientation the gear 54, and associated supply spool 58, are prohibited from rotation. Alternatively, when the thumb slide 64 is in the second orientation the gear 54, and associated supply spool 58, are permitted to freely rotate.

TAKE-UP ARM

The take-up arm 66 is defined by a forward end 68, a rearward end 72 and an intermediate extent therebetween. The take-up arm 66 is further defined by an outer edge 74, an inner edge 76 an upper surface and a lower surface. As with the supply arm, the take-up arm 66 is curved at its forward end 68. Furthermore, a semicircular extension 78 is formed on the inner edge 76 of the take-up arm 66 at the intermediate extent. Additionally, a spring support 82 is formed on the inner edge 76 of the take-up arm 66 intermediate the semicircular extension 78 and the rearward end 72. The function of the semicircular extension 78 and spring support 82 will be described in greater detail hereinafter.

A floss channel 84 is formed within the upper surface of the take-up arm 66 and extends from adjacent the semicircular extension 78 to the forward end 68. Additionally, a number of floss guides are formed along the floss channel 84. Each of these floss guides are blocks with a floss guiding passage formed therein. In an alternative embodiment, each of the floss channels 84 and 36 have a rearward extent upon the top of the respective arm, and a forward extent within the side of the respective arm. In this manner the floss is routed along the side of each respective arm.

A circular recess is formed within the upper surface of the take-up arm 66 adjacent the semicircular extension. This circular recess defines an interior area. This interior area, and associated recess, will be described in greater detail with respect to the take-up assembly 96. A number of recess are formed within the outer edge 74 of the take-up arm 66 in between the intermediate extent and the rearward end 72. At least one of these recesses 86 constitutes a loading orientation recess and at least one of the recesses 86 constitutes a use orientation recess. In the preferred embodiment, there are two such recesses 86, one being the loading orientation recess 88 and the other being the use orientation recess 92. The exact function of these recesses 86 will be described in greater detail hereinafter.

FLOSS TAKE-UP ASSEMBLY

A floss take-up assembly is associated with the take up arm. In general, the take-up assembly is similar in construction to the floss supply assembly, note FIG. 3. This assembly includes a shaft integrally formed within the interior area of the take-up arm. The assembly further includes a cylindrical geared shaft cover which is, in part, defined by an upper peripheral edge and a lower peripheral edge. A gear is integrally formed with the shaft cover adjacent the lower peripheral edge. Furthermore, a plurality of locking notches are formed within the upper peripheral edge. The shaft cover is positioned over the shaft such that the lower peripheral edge fits into the circular recess of the take-up arm. A spring member is positioned within the take-up arm adjacent the outer edge and proximate the intermediate extent. This spring member functions to engage the gear of the shaft cover. This engagement permits the rotation of the take-up spool only in a clockwise sense. The assembly further includes a take-up spool. This take-up spool is defined by an upper circular plate, a lower circular plate and a cylindrical extent therebetween. A floss receiving notch is formed within the upper circular plate. The cylindrical extent includes an interior area, with a plurality of locking protrusions extending from this interior area. The number and position of the protrusions corresponding to the number and position of the locking notches. As with the supply assembly, a spring can be employed in between the take-up spool and the shaft cover. Additionally, means can be employed to vary the distribution of the floss over the take up spool. In part, this means would include a ramped surface formed below the gear of the shaft cover. This ramped surface would cooperate with a matching ramped surface formed within the take up arm. In this manner, rotation of the shaft cover would effect a repeating up and down linear motion of the spool. Thus, the floss received upon the spool would be evenly distributed.

Thus, the take-up spool is adapted to be fitted over the shaft cover such that the locking notches engage the locking protrusions. This engagement is similar to the engagement between the supply spool and its associated shaft cover.

As is illustrated in FIG. 1, the supply arm and take-up arm are pivotally interconnected by way of the semicircular extension of the supply arm and the semicircular extension of the take-up arm. This interconnection can be achieved by way of a rivet or the like. Furthermore, a spring serves to interconnect the spring support of the supply arm and the spring support of the take-up arm. Lastly, a band 94 is adapted to be positioned within one of the recesses of the supply arm and one of the recesses of the take-up arm. The device is in a loading orientation when the band 94 is positioned within loading orientation recesses of the two arms. Alternatively, the device is in the use orientation when the band 94 is positioned within the use orientation recesses of the two arms. Depending upon the depth of the respective recess, a tightening or loosening of any dental floss positioned between the two arms can be effected by the positioning of the band.

With respect to materials, each of the arms are preferably constructed from solid plastic. Furthermore, a rubberized coating is preferably employed at the forward ends of the arms. This coating lessens any accidental impact between the arms and the interior of the users mouth. Furthermore, this rubberized coating can be employed at the outer edge of the rearward end of each arm. Here, the coating allows a user to maintain a proper grip upon the device. Additionally, the plastic portion of the device can be produced in a variety of colors. Directional arrows can be formed upon the upper surface of each arm to instruct a user how to properly install the dental floss.

OPERATION OF THE DEVICE

In use, an operator of the device first places a new supply spool of dental floss upon the shaft cover of the supply assembly. The details of this connection is described in greater detail hereinabove. The thumb slide is place in its second orientation such that rotation of the supply spool can be achieved. At this point, the operator should ensure that the device is in its loading orientation. More specifically, the band is slid such that it engages the loading recesses. Dental floss is then routed from the supply spool, through the respective channels and guides, to the take-up spool. Here, the end of the dental floss is affixed within a roughened, sandblasted and/or beaded notch formed upon the take-up spool. The take-up spool is then rotated in a clockwise fashion several times. At this point, the thumb slide is slid back into the first orientation to prohibit further rotation of the supply spool. Next, the band is slid to the use orientation. The device is now ready for use by the operator. There are several modifications that can be incorporated in the present invention to decrease its profile, and thereby, facilitate its use within the mouth. For example, the forward portion of both the supply and take up arms can be linear as opposed to curved. Furthermore, both the floss supply and floss take up assemblies can be recessed with respect to the remainder of the device. The recessed assemblies, as well as the linear forward extents of the arms, would give the entire device a thinner profile. In the preferred embodiment, the loading orientation recesses are formed so as to create a fork width of approximately 20 mm. Alternatively, the use orientation recesses are formed so as to create a fork width of between 21–25 mm.

Turning now to the dimensions of the device, in the preferred embodiment, the length of the device is 13 cm. Furthermore, the overall width of the device, as measured across the bobbin and spool areas is 3.5 cm. The floss supply assembly is 7 mm high, with the supply spool having a diameter of 16 mm. The take-up assembly is between 7–8 mm high with the take-up spool having a diameter of 14 mm.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A flossing device having a floss loading orientation and a floss use orientation, the device comprising in combination:

a supply arm having a forward end, a rearward end and an intermediate extent therebetween, the supply arm further including an outer edge, an inner edge an upper surface and a lower surface, a semicircular extension formed on the inner edge of the supply arm at the intermediate extent, a spring support formed on the inner edge of the supply arm intermediate the semicircular extension and the rearward end, a floss channel formed within the upper surface of the supply arm and extending from adjacent the semicircular extension to the forward end, a number of floss guides formed along the floss channel, a circular recess formed within the upper surface of the supply arm adjacent the semicircular extension, the circular recess defining an interior area, a number of recess formed within the outer edge of the supply arm in between the intermediate extent and the rearward end, at least one of the recesses constituting a loading orientation recess and at least one of the recesses constituting a use orientation recess;

a floss supply assembly associated with the supply arm, the floss supply assembly comprising a shaft integrally formed within the interior area of the supply arm, a cylindrical geared shaft cover having an upper peripheral edge and a lower peripheral edge, a gear formed integrally with the shaft cover adjacent the lower peripheral edge, a plurality of locking notches formed within the upper peripheral edge, the shaft cover positioned over the shaft such that the lower peripheral edge fits into the circular recess of the supply arm, a supply spool having an upper circular plate, a lower circular plate and a cylindrical extent therebetween, the cylindrical extent having an interior area, a plurality of locking protrusions extending from the interior area of the cylindrical extent of the supply spool, the number and position of the protrusions corresponding to the number and position of the locking notches, the supply spool adapted to be fitted over the shaft cover such that the locking notches engage the locking protrusions, a supply of dental floss supplied upon the supply spool, a thumb slide slidable provided within the upper surface of the supply arm adjacent the shaft, the thumb slide having a forward gear engaging end, the thumb slide having a first orientation wherein the first end is engaged with the gear of the shaft cover and a second orientation wherein the first end is disengaged from the gear of the shaft cover;

a take-up arm having a forward end, a rearward end and an intermediate extent therebetween, the take-up arm further including an outer edge, an inner edge an upper surface and a lower surface, a semicircular extension formed on the inner edge of the take-up arm at the intermediate extent, a spring support formed on the inner edge of the take-up arm intermediate the semicircular extension and the rearward end, a floss channel formed within the upper surface of the take-up arm and extending from adjacent the semicircular extension to the forward end, a number of floss guides formed along the floss channel, a circular recess formed within the upper surface of the take-up arm adjacent the semicircular extension, the circular recess defining an interior area, a number of recess formed within the outer edge of the take-up arm in between the intermediate extent and the rearward end, at least one of the recesses constituting a loading orientation recess and at least one of the recesses constituting a use orientation recess;

a floss take-up assembly associated with the take up arm, the floss take-up assembly comprising a shaft integrally formed within the interior area of the take-up arm, a cylindrical geared shaft cover having an upper peripheral edge and a lower peripheral edge, a gear formed integrally with the shaft cover adjacent the lower peripheral edge, a plurality of locking notches formed within the upper peripheral edge, the shaft cover positioned over the shaft such that the lower peripheral edge fits into the circular recess of the take-up arm, a take-up spool having an upper circular plate, a lower circular plate and a cylindrical extent therebetween, the cylindrical extent having an interior area, a plurality of locking protrusions extending from the interior area of the cylindrical extent of the take-up spool, the number and position of the protrusions corresponding to the number and position of the locking notches, the take-up spool adapted to be fitted over the shaft cover such that the locking notches engage the locking protrusions;

the supply arm and take-up arm being pivotally interconnected by way of the semicircular extension of the supply arm and the semicircular extension of the take-up arm, a spring interconnecting the spring support of the supply arm and the spring support of the take-up arm, a band adapted to be positioned within one of the recesses of the supply arm and one of the recesses of the take-up arm, the device being in a loading orientation when the band is positioned within loading orientation recesses, and the device being in a use orientation when the band is positioned within use orientation recesses.

2. A flossing device having a floss loading orientation and a floss use orientation, the device comprising in combination:

a supply arm having a forward end, a rearward end and an intermediate extent therebetween, the supply arm further including an outer edge, an inner edge an upper surface and a lower surface, an extension formed on the inner edge of the supply arm at the intermediate extent, a floss channel formed within the upper surface of the supply arm and extending from adjacent the extension to the forward end, a number of recess formed within the outer edge of the supply arm in between the intermediate extent and the rearward end, at least one of the recesses constituting a loading orientation recess and at least one of the recesses constituting a use orientation recess;

a floss supply assembly associated with the supply arm;

a take-up arm having a forward end, a rearward end and an intermediate extent therebetween, the take-up arm further including an outer edge, an inner edge an upper surface and a lower surface, an extension formed on the inner edge of the take-up arm at the intermediate extent, a floss channel formed within the upper surface of the take-up arm and extending from adjacent the extension to the forward end, a number of recess formed within the outer edge of the take-up arm in between the intermediate extent and the rearward end, at least one of the recesses constituting a loading orientation recess and at least one of the recesses constituting a use orientation recess;

a floss take-up assembly associated with the take up arm;

the supply arm and take-up arm being pivotally interconnected by way of the extension of the supply arm and the extension of the take-up arm, a band adapted to be positioned within one of the recesses of the supply arm and one of the recesses of the take-up arm, the device being in a loading orientation when the band is positioned within loading orientation recesses, and the device being in a use orientation when the band is positioned within use orientation recesses.

3. The device as described in claim 2 wherein:

the floss supply assembly comprises a shaft integrally formed upon the supply arm, a cylindrical geared shaft cover having an upper peripheral edge and a lower peripheral edge, a gear formed integrally with the shaft cover adjacent the lower peripheral edge, a plurality of locking notches formed within the upper peripheral edge, the shaft cover positioned over the shaft such that the lower peripheral edge fits into a circular recess within the supply arm, a supply spool having an upper circular plate, a lower circular plate and a cylindrical extent therebetween, the cylindrical extent having an interior area, a plurality of locking protrusions extending from the interior area of the cylindrical extent of the supply spool, the number and position of the protrusions corresponding to the number and position of the locking notches, the supply spool adapted to be fitted over the shaft cover such that the locking notches engage the locking protrusions, a supply of dental floss supplied upon the supply spool, a thumb slide slidable provided within the upper surface of the supply arm adjacent the shaft, the thumb slide having a forward gear engaging end, the thumb slide having a first orientation wherein the first end is engaged with the gear of the shaft cover and a second orientation wherein the first end is disengaged from the gear of the shaft cover; and the floss take-up assembly comprises a shaft integrally formed on the take-up arm, a cylindrical geared shaft cover having an upper peripheral edge and a lower peripheral edge, a gear formed integrally with the shaft cover adjacent the lower peripheral edge, a plurality of locking notches formed within the upper peripheral edge, the shaft cover positioned over the shaft such that the lower peripheral edge fits into a circular recess within the take-up arm, a take-up spool having an upper circular plate, a lower circular plate and a cylindrical extent therebetween, the cylindrical extent having an interior area, a plurality of locking protrusions extending from the interior area of the cylindrical extent of the take-up spool, the number and position of the protrusions corresponding to the number and position of the locking notches, the take-up spool adapted to be fitted over the shaft cover such that the locking notches engage the locking protrusions.

4. The device as described in claim 2 further comprising:.

a spring support formed on the inner edge of the supply arm intermediate the extension and the rearward end; and a spring support formed on the inner edge of the take-up arm intermediate the extension and the rearward end; and a spring interconnecting the spring support of the supply arm and the spring support of the take-up arm.

* * * * *